United States Patent [19]

Miyazawa et al.

[11] Patent Number: 5,080,827
[45] Date of Patent: Jan. 14, 1992

[54] 1,2-PROPANEDIOL DERIVATIVE

[75] Inventors: Kazutoshi Miyazawa; Shinichi Saito; Kouji Ohno; Hiromichi Inoue; Makoto Ushioda, all of Kanagawa, Japan

[73] Assignee: Chisso Corporation, Ohsaka, Japan

[21] Appl. No.: 572,356

[22] Filed: Aug. 24, 1990

Related U.S. Application Data

[63] Continuation of Ser. No. 154,212, Feb. 10, 1988, abandoned.

[30] Foreign Application Priority Data

Feb. 16, 1987 [JP] Japan .................. 62-32654

[51] Int. Cl.$^5$ ............... C09K 19/12; C07C 69/66; C07C 43/11
[52] U.S. Cl. .................. 252/299.66; 252/299.6; 252/299.01; 560/187; 568/609; 568/610
[58] Field of Search ........... 252/299.01, 299.6, 299.66; 560/187; 568/609, 610

[56] References Cited

U.S. PATENT DOCUMENTS

| | | | |
|---|---|---|---|
| 4,556,727 | 12/1985 | Walba | 252/299.01 |
| 4,725,688 | 2/1988 | Taguchi et al. | 252/299.61 |
| 4,744,918 | 5/1988 | Hepple et al. | 252/299.61 |
| 4,966,727 | 10/1990 | Ichihashi et al. | 252/299.66 X |
| 4,973,426 | 11/1990 | Ohno et al. | 252/299.66 |
| 4,985,172 | 1/1991 | Wingen et al. | 252/299.66 X |
| 5,013,475 | 5/1991 | Shibata et al. | 252/299.01 X |

FOREIGN PATENT DOCUMENTS

| | | | |
|---|---|---|---|
| 255219 | 2/1988 | European Pat. Off. | |
| 279629 | 8/1988 | European Pat. Off. | 252/299.66 |
| 322862 | 7/1989 | European Pat. Off. | 252/299.66 |
| 332025 | 9/1989 | European Pat. Off. | 252/299.66 |
| 3515373 | 11/1986 | Fed. Rep. of Germany | 252/299.61 |
| 63-51377 | 3/1988 | Japan | 252/299.61 |
| 63-255264 | 10/1988 | Japan | 252/299.66 |
| 01006239 | 1/1989 | Japan | 252/299.66 |
| 02067252 | 3/1990 | Japan | 252/299.66 |
| WO86/2937 | 5/1986 | World Int. Prop. O. | 252/299.6 |
| 87/5012 | 8/1987 | World Int. Prop. O. | |

OTHER PUBLICATIONS

Emoto, N. et al., Jpn. J. Appl. Phys., Part 2, 28(1) L121, 1989.

Primary Examiner—John S. Maples
Assistant Examiner—Richard Treanor
Attorney, Agent, or Firm—Wenderoth, Lind & Ponack

[57] ABSTRACT

An optically active compound particularly useful as a component of liquid crystal compositions having a high response rate and a chiral liquid crystal composition containing the same are provided, which optically active compound is expressed by the formula (I)

$$R^1-\boxed{A}-\boxed{B}-O\overset{*}{C}H(CH_3)CH_2O-(C(=O))_m-(\overset{*}{C}H(CH_3)O)_n-R^2 \quad (I)$$

wherein $R^1$ represents alkyl or alkoxy each of 1-20 C, H, halogen or CN;

$-\boxed{A}-$ and $-\boxed{B}-$ each represent a specified six-membered ring; $R^2$ represents alkyl of 1-20 C; the asterisk designates an asymmetric carbon atom; and m and n each represents 0 or 1.

8 Claims, No Drawings

1,2-PROPANEDIOL DERIVATIVE

This application is a continuation of now abandoned application, Ser. No. 07/154,212 filed on Feb. 10, 1988.

BACKGROUND OF THE INVENTION

1. Field of the Invention

This invention relates to a novel optically active compound and a liquid crystal composition containing the same. More particularly it relates to an optically active compound having a similar structure to those of liquid crystal compounds and a chiral liquid crystal composition containing the same.

2. Description of the Related Art

At present, TN (Twisted Nematic) type display mode has been most broadly employed, but it is inferior in the response rate to emissive type display elements (electroluminescence, plasma display, etc.), and various improvements in this respect have been attempted. However, it does not appear that there is much possibility remaining for improvement to a large extent. Thus, various liquid crystal devices based on another principle in place of that of TN type display element have been attempted, and among these, there is a display method using ferroelectric liquid crystals (N.A. Clark et al, Applied Phys. lett., 36, 899 (1980)). This mode utilizes ferroelectric liquid crystal chiral smectic C phase (hereinafter abbreviated to SC* phase) or other chiral smectic phases such as SH* phase, SF* phase, SG* phase, etc., and the mode has the following three superior specific features as compared with TN type display mode:

- a first specific feature consists in that it has a very high response rate amounting to 100 times the response rate of TN type display element; a second specific feature consists in that it has a memory effect to make the multiplex drive easy in combination with the above-mentioned high response rate; and a third specific feature consists in that the gray scale can be more easily obtained, only by controlling the inversion time of its polarity, as compared with TN type display mode, and hence it has been said that the mode is suitable for graphic display.

However, in spite of its superior features, as to ferroelectric liquid crystals and compositions currently known, no sufficiently satisfactory results in the aspect of response rate have yet been obtained; thus it appears that this mode has reached a deadlock in terms of its practical aspect use. The reason is considered to be due to the fact that development of a liquid crystal compound having a very high response rate has not been realized.

SUMMARY OF THE INVENTION

The object of the present invention is to provide an optically active compound having specific features suitable to the above-mentioned display mode and particularly useful as a component of liquid crystal compositions having a high response rate, and a chiral liquid crystal composition containing the compound.

The present invention resides in;

an optically active compound expressed by the formula

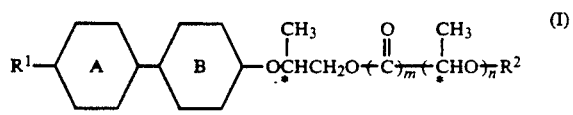

wherein $R^1$ represents an alkyl group or alkoxy group each of 1 to 20 carbon atoms, hydrogen atom, a halogen atom or cyano group;

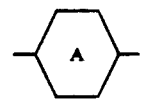

and

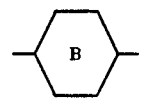

each represent

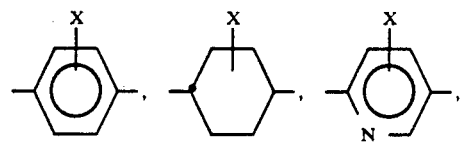

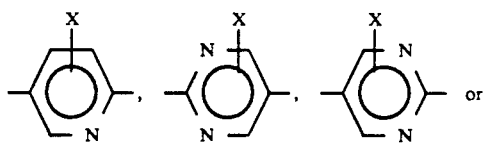

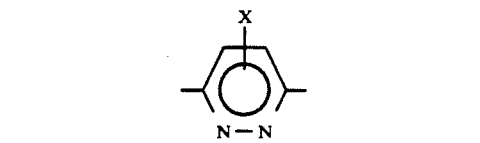

wherein X represents hydrogen atom, a halogen atom or cyano group; $R^2$ represents an alkyl group of 1 to 20 carbon atoms; the asterisk designates an asymmetric carbon atom; and m and n each represent 0 or 1, and a chiral liquid crystal composition containing the same.

In the above formula (I), $R^1$ is preferably an alkyl group or alkoxy group each of 4 to 16 carbon atoms, more preferably those each of 6 to 12 carbon atoms; $R^2$ is preferably an alkyl group of 2 to 10 carbon atoms, more preferably that of 3 to 8 carbon atoms; as to m and n, a combination of m=1 with n=0 is most preferable and that of m=1 with n=01 and that of m=0 with n=0 are also preferable; and preferred examples of combinations of

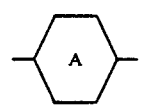

with

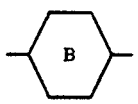

are

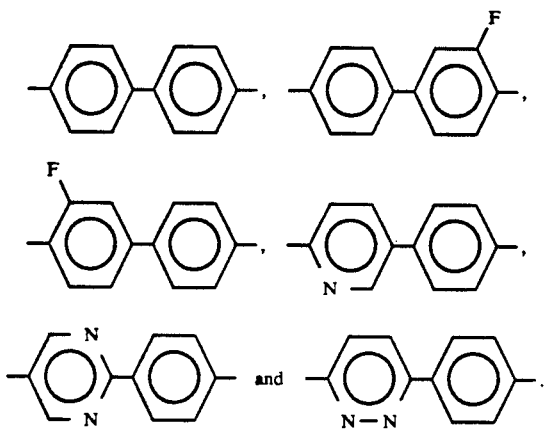

DETAILED DESCRIPTION OF PREFERRED EMBODIMENTS

Most of the compounds of the formula (I) exhibit no liquid crystal phase by itself, but when it is added in a suitable amount to another compound having smectic C phase, it is possible to obtain a chiral smectic liquid crystal composition having a very high response rate. This means that the compound of the formula (I) has a capability of potentially accelerating the response rate; hence the compound can be said to be far superior as a component of ferroelectric liquid crystal compositions.

For example, as described in the following Examples, when the compound of the formula (I) of the present invention is added in an amount of 20% by weight to liquid crystal compositions having achiral smectic C phase, it is possible to obtain a response rate as high as 125 μsec at 25° C.

Or, when the compound of the formula (I) of the present invention is added in a suitable amount to compositions exhibiting chiral smectic C phase but having a very low response rate, it is possible to obtain chiral smectic liquid crystal compositions having a practical response rate.

Further, as to the chiral pitch of chiral nematic liquid crystal compositions containing the compound of the present invention, for example, when the compound of Example 1 of the present invention was added in an amount 1% by weight to ZLI-1132 manufactured by Merck Company the chiral pitch of the resulting mixture was measured to give a pitch as short as 29 μm; hence it is seen that the compound of the present invention is very useful as a pitch-adjusting agent for chiral nematic liquid crystal compositions.

Further, its temperature dependency δp is very good and those expressed by the equation $$\delta p = \frac{2(P(t_1) - P(t_2))}{P(t_1) + P(t_2)} \times \frac{100}{t_1 - t_2}$$

wherein $t_1$ and $t_2$ each represent temperature and $P(t)$ represents pitch at t° C., were as very small as 0.54 at $t_1 = 20°$ C. and at $t_2 = 70°$ C.

The resulting characteristics can be said to be surprising in view of the fact that the δp of for example a currently known pitch-adjusting agent for chiral nematic liquid crystal compositions, (S)-4-(2'-methylbutyloxy)-4'-cyanobiphenyl, is 1.001 as measured under the same conditions.

In addition, the compound of the formula (I) has an optically active asymmetric carbon atom; hence when it is added to nematic liquid crystals, it has a capability of inducing a twisted structure. Since nematic liquid crystals having a twisted structure, i.e., chiral nematic liquid crystals do not form the so-called reverse domain of TN type display elements, the compound of the formula (I) is also usable as an agent for preventing reverse domain from forming.

Next, preparation of the compound of the formula (I) will be described. The compound may be preferably prepared by the following route:

(i) In the case of M=1:

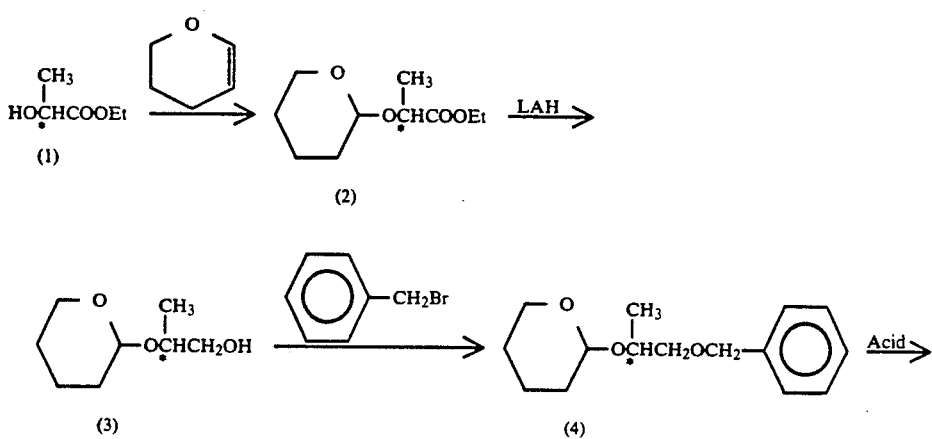

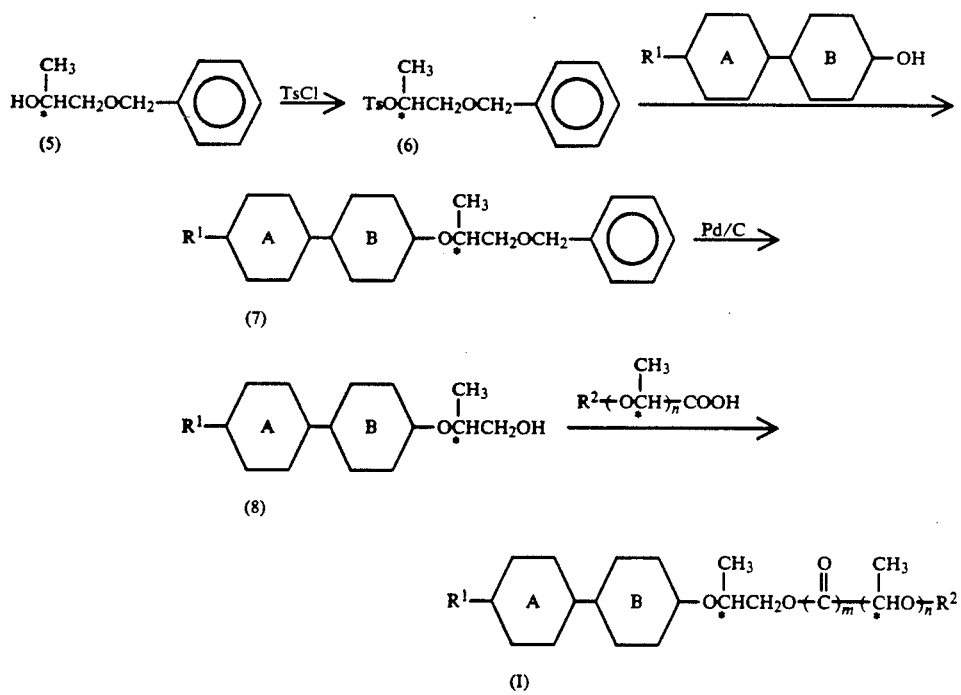

In the above equations, $R^1$, $R^2$,

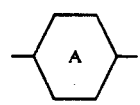

and

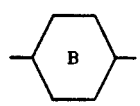

are as defined above.

Namely, dihydropyran is reacted with ethyl lactate (1) to obtain a compound (2), which is reduced with a reducing agent such as lithium aluminum hydride to obtain a compound (3), into which a protecting group such as a benzyl group is introduced to obtain a compound (4), which is reacted with an acid to obtain a compound (5), into which an elimination group such as a tosyl group is introduced to obtain a compound (6), which is reacted with a phenol to obtain a compound (7), from which the protecting group is freed with a reducing agent to obtain a compound (8), which is reacted with a carboxylic acid corresponding to the final objective compound to obtain a compound of the formula (I).

(ii) In the case of m=0:

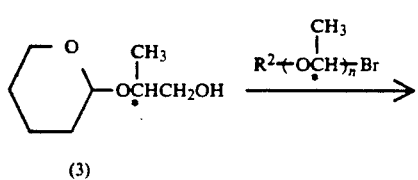

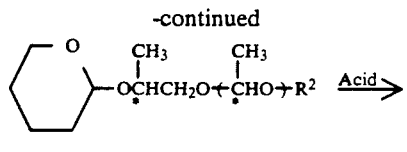

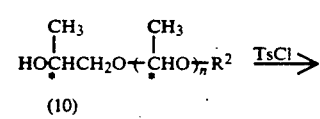

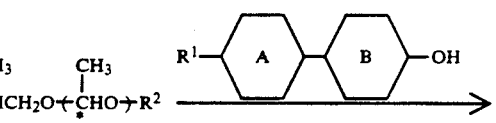

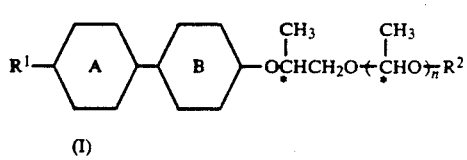

In the above equations, $R^1$, $R^2$,

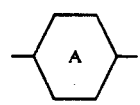

and

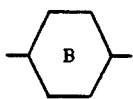

are as defined above.

Namely, an alkyl group is introduced into the compound (3) prepared in the above (i) to obtain a compound (9), which is reacted with an acid to obtain a compound (10), into which an elimination group such as a tosyl group is introduced to obtain a compound (11), which is reacted with a phenol corresponding to the final objective compound to obtain a compound of the formula (I).

Representative compounds among those prepared according to the above-mentioned processes will be illustrated below:

4-(2'-hexanoyloxy-1'-methyl)ethyloxy-4'-octyloxybiphenyl 4-(2'-heptanoyloxy-1'-methyl)ethyloxy-4'-octyloxybiphenyl (Example 1, m.p. 52° C.)

4-(2'-octanoyloxy-1'-methyl)ethyloxy-4'-octylbiphenyl 4-fluoro-4-(2'-hexanoyloxy-1'-methyl)ethyloxy-4'-octyloxybiphenyl 3-fluoro-4-(2'-heptanoyloxy-1'-methyl)ethyloxy-4'-octyloxybiphenyl 3-fluoro-4-(2'-octanoyloxy-1'-methyl)ethyloxy-4'-octylbiphenyl 3-fluoro-4-octyloxy-4'-(2''-pentanoyloxy-1''-methyl)ethyloxybiphenyl 3-fluoro-4-hexyloxy-4'-(2''-hexanoyloxy-1''-methyl)ethyloxybiphenyl 4-[1'-methyl-2'-(4''-methylpentanoyloxy)]ethyloxy-4'-octyloxybiphenyl (Example 2, m.p. 40.8° C.)

4-[1'-methyl-2'-(4''-methylhexanoyloxy)]ethyloxy-4'-octyloxybiphenyl 3-fluoro-4-[1'-methyl-2'-(4''-methylhexanoyloxy)]-ethyloxy-4'-octyloxybiphenyl 3-fluoro-4-[1'-methyl-2'-(4''-methylhexanoyloxy)]-ethyloxy-4'-octylbiphenyl 4-[2'-(2''-butyloxypropanoyloxy)-1'-methyl]ethyloxy-4'-octyloxybiphenyl (Example 4, m.p. 21.0° C.; Example 5, m.p. 32.5° C.)

4-[2'-(2''-hexyloxypropanoyloxy)-1'-methyl]ethyloxy-4'-heptylbiphenyl

4-[1'-methyl-2'-(4''-methylhexanoyloxy)]ethyloxy-4'-octyloxybiphenyl (Example 3, m.p. 40.5° C.)

4-[1'-methyl-2'-(4''-methylheptanoyloxy)]ethyloxy-4'-hexylbiphenyl 4-(2'-butyloxy-1'-methyl)ethyloxy-4'-octyloxybiphenyl (Example 6, m.p. 39.6° C.)

4-(2'-pentyloxy-1'-methyl)ethyloxy-4'-heptylbiphenyl 5-octyl-2-[4'-(2''-heptanoyloxy-1''-methyl)ethyloxy]-phenylpyridine 5-heptyl-2-[4'-(2''-pentanoyloxy-1''-methyl)ethyloxy]-phenylpyridine 5-octyl-2-{4'-[2''-(2'''-butyloxypropanoyloxy)-1''methyl]ethyloxy}phenylpyridine 5-hexyl-2-[4'-(2''-heptanoyloxy-1''-methyl)ethyloxy]-phenylpyrimidine 5-heptyl-2-{4'-[2''-(2'''-hexyloxypropanoyloxy)-1''-methyl]ethyloxy}phenylpyrimidine 3-octyl-6-[4'-(2''-heptanoyloxy-1''-methyl)-ethyloxy]-phenylpyridazine 3-nonyl-6-{4'-[2''-(2'''-pentyloxypropanoyloxy)-1''-methyl]ethyloxy}phenylpyridazine 4-octyl-trans-cyclohexyl-4'-[(2''-hexanoyloxy-1-methyl)ethyloxy]benzene 4-octyl-trans-cyclohexyl-4'-[2''-(2'''-butyloxypropanoyloxy)-1''-methyl]ethyloxybenzene 2-(4'-hexyloxyphenyl)-5-((1'-methyl-2'-butoxy)-ethyloxy)pyrimidine 2-(4'-nonyloxyphenyl)-5-((1'-methyl-2'-butanoyloxy)-ethyloxy)pyrimidine 2-(4'-octyloxyphenyl)-5-((1'-methyl-2'-(2''-butoxypropanoyloxy)-ethyloxy)pyrimidine The optically active compound of the present invention will be described in more detail by way of Examples.

EXAMPLE 1

Preparation of (R)-4-(2'-heptanoyloxy-1'-methyl)-ethyloxy-4'-octyloxybiphenyl (a compound of the formula (I) wherein $R^1 = C_8H_{17}O$, $R^2 = C_6H_{13}$—,

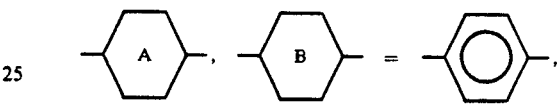

$m = 1$ and $n = 0$)

(S)-1-hydroxy-2-tetrahydropyranyloxypropane (120 g, 0.75 mol) prepared according to the method of C. Malanga et al, Synthetic Communications, 12,(1), 67–70 (1982)) was dropwise added to sodium hydride (44.8 g, 1.87 mol) in tetrahydrofuran (400 ml) (hereinafter abbreviated to THF), followed by adding dimethylformamide (hereinafter abbreviated to DMF) (200 ml), agitating the mixture for 2 hours, dropwise adding benzyl bromide (140.8 g, 0.82 mol) at 30° C. or lower, agitating the mixture at room temperature for 6 hours, adding toluene, sufficiently agitating the mixture, washing the resulting organic layer with 2N-NaOH aqueous solution and then with water, drying it over anhydrous magnesium sulfate, distilling off toluene, adding to the resulting oily residue, (S)-1-benzyloxy-2-tetrahydropyranyloxypropane, pyridium p-toluenesulfonate (18 g) and ethanol (500 ml), heating the mixture to 70° C. for one hour, distilling off ethanol, adding toluene to the residue, sufficiently washing it with water, distilling off toluene, and distilling the residue to obtain (S)-1-benzyloxy-2-hydroxypropane (98 g)(b.p. 94.0° C./2.5 mmHg). A mixture of this (S)-1-benzyloxy-2-hydroxypropane (60 g, 0.36 mol) with anhydrous pyridine (300 g) was cooled with ice, followed by dropwise adding a solution of p-toluenesulfonyl chloride (75.8 g, 0.20 mol) in pyridine (70 ml) at 0° C., agitating the mixture at room temperature for 3 hours, adding toluene (800 ml), agitating the mixture, several times washing the resulting organic layer with water, drying it over anhydrous magnesium sulfate and distilling off toluene to obtain (S)-1-benzyloxy-2-(p-toluenesulfonyloxy)propane (115.2 g). On the other hand, a solution of 4-hydroxy-4'-octyloxybiphenyl (50 g, 0.17 mol) in THF (200 ml) was dropwise added to a mixture of sodium hydride (8.5 g, 0.35 mol) with THF (100 ml), followed by dropwise adding a solution of the above (S)-1-benzyloxy-2-(p-toluenesulfonyloxy)propane (64.5 g)(0.20 mol) in DMF (100 ml), agitating the mixture at 60° C. for 4 hours, allowing the mixture to cool down, adding toluene, agitating the mixture, washing with 6N-HCl, then with 2N-NaOH and further with water, drying over anhydrous magnesium sulfate, distilling off toluene, dissolving the residue in a mixture of ethanol (250 ml) with ethyl acetate (250 ml), adding Pd/C catalyst (10 g), agitating the mixture in hydrogen gas, filtering off the Pd/C, distilling off the solvent, and recrystallizing the residue from heptane (150 ml), to obtain (R)-4-(2'-hydroxy-1'-methyl)ethyloxy-4'-octyloxybiphenyl (m.p. 107.9° C.).

This (R)-4-(2'-hydroxy-1'-methyl)ethyloxy-4'-octyloxy-biphenyl (10 g, 0.028 mol) and heptanoic acid (9.1 g, 0.07 mol) were dissolved in dichloromethane (300 ml), followed by adding to the solution, dicyclohexylcarbodiimide (hereinafter abbreviated to DCC) (17.3 g, 0.084 mol) and dimethylaminopyridine (hereinafter abbreviated to DMAP) (2.7 g), agitating the mixture at room temperature for 2 hours, filtering off deposited crystals, distilling off the solvent and recrystallizing the residue from ethanol (150 ml) to obtain the objective (R)-4-(2'-heptanoyloxy-1'-methyl)ethyloxy-4'-octyloxybiphenyl (6.0 g) (m.p. 52.0° C.).

EXAMPLE 2

Preparation of (R)-4-[1'-methyl-2'-(4''-methyl-pentanoyloxy)]ethyloxy-4'-octyloxybiphenyl (a compound of the formula (I) wherein $R^1 = C_8H_{17}O-$; $R^2 = (CH_3)_2CH_2CH_2CH_2-$;

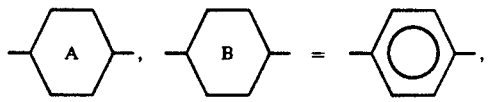

m = 1; and n = 0)

(R)-4-(2'-hydroxy-1'-methyl)ethyloxy-4'-octyloxybiphenyl (10 g, 0.28 mol) prepared in Example 1 and isocaproic acid (8.1 g, 0.07 mol) were dissolved in dichloromethane (300 ml), followed by adding to the solution, DDC (17.3 g, 0.084 mol) and DMAP (2.7 g), agitating the mixture at room temperature for 2 hours, filtering off deposited crystals, distilling off the solvent and recrystallizing the residue from ethanol (150 ml) to obtain (R)-4-[1'-methyl-2'-(4''-methylpentanoyloxy)]ethyloxy-4'-octyloxybiphenyl (7.1 g) (m.p. 40.8° C.).

EXAMPLE 3

Preparation of 4-[1'-(R)-methyl-2'-(4''-(S)-methylhexanoyloxy)]ethyloxy-4'-octyloxybiphenyl (a compound of the formula (I) wherein $R^1 = C_8H_{17}O-$,

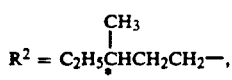

$$R^2 = C_2H_5\overset{*}{C}HCH_2CH_2-,$$

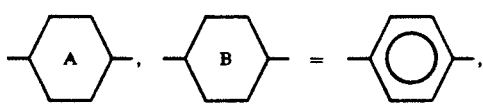

m = 1 and n = 0)

(R)-4-(2'-hydroxy-1'-methyl)ethyloxy-4'-octyloxybiphenyl (10 g, 0.28 mol) prepared in Example 1 and (S)-4-methylhexanoic acid (9.1 g, 0.07 mol) were dissolved in dichloromethane (300 ml), followed by adding to the solution, DCC (17.3 g, 0.084 mol) and DMAP (2.7 g), agitating the mixture at room temperature for 2 hours, filtering off deposited crystals, distilling off the solvent and recrystallizing the residue from ethanol (150 ml) to obtain 4-[1'-(R)-methyl-2'-(4''-(S)- methylhexanoyloxy)] ethyloxy-4'-octyloxybiphenyl (6.9 g) (m.p. 40.5° C.).

EXAMPLE 4

Preparation of 4-[2'-(2''-(S)-butyloxypropanoyloxy)-1'-(R)-methyl]ethyloxy-4'-octyloxybiphenyl (a compound of the formula (I) wherein $R^1 = C_8H_{17}O-$, $R^2 = C_4H_9$,

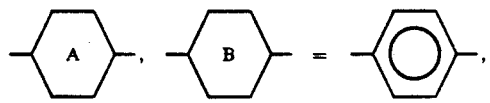

m = 1 and n = 1)

(i) Preparation of (S)-2-butyloxypropionic acid:

Silver oxide (77.5 g, 0.3 mol) was added to a mixture of ethyl L-(+)-lactate (49.4 g, 0.4 mol) with 1-iodobutane (100 g, 0.5 mol) over 2 hours, followed by allowing the mixture to stand at room temperature for 3 days, adding ether (30 ml) to dilute it, filtering, distilling off ether, washing the residue with 2N-NaOH aqueous solution, drying it over anhydrous magnesium sulfate and distilling it to obtain ethyl (S)-2-butyloxypropionate (30.7 g) (b.p. 64° C./7 mmHg), adding to this product, 5N-NaOH aqueous solution (50 ml), agitating the mixture at room temperature for 5 hours, pouring it in 6N-HCl (75 ml), adding ether, agitating the mixture, washing the resulting organic layer with water and distilling off ether to obtain (S)-2-butyloxypropionic acid (21.4 g).

(ii) Preparation of the objective product:

(R)-4-(2'-hydroxy-1'-methyl)ethoxy-4'-octylbiphenyl (10 g, 0.28 mol) prepared in Example 1 and (S)-2-butyloxypropionic acid (10.2 g, 0.07 mol) obtained in the above (i) were dissolved in dichloromethane (300 ml), followed by adding DCC (17.3 g, 0.084 mol) and DMAP (2.7 g), agitating the mixture at room temperature for 2 hours, filtering off deposited crystals, distilling off the solvent and recrystallizing the residue from ethanol (150 ml) to obtain the objective 4-[2'-(2''-(S)-butyloxypropanoyloxy)-1'-(R)-methyl]ethyloxy-4'-octyloxybiphenyl (7.2 g) (m.p. 21.0° C.).

EXAMPLE 5

Preparation of 4-[2'-(2''-(R)-butyloxypropanoyloxy)-1'-(R)-methyl]ethyloxy-4'-octyloxybiphenyl (a compound of R-form in place of (S)-form of the compound of Example 4)

Example 4 was repeated except that (R)-2-butyloxypropionic acid was used in place of (S)-2-butyloxypropionic acid to obtain 4-[2'-(2''-(R)-butyloxypropanoyloxy)-1'-(R)-methyl]ethyloxy-4'-octyloxybiphenyl (8.2 g) (m.p. 32.5° C.).

(R)-2-butyloxypropionic acid used herein may be prepared using methyl D-(-)-lactate in place of ethyl L-(+)-lactate used in Example 4.

EXAMPLE 6

Preparation of (R)-4-(2'-butyloxy-1'-methyl)-ethyloxy-4'-octyloxybiphenyl (a compound of the formula (I) wherein $R^1 = C_8H_{17}O-$, $R^2 = C_4H_9-$,

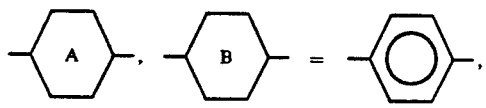

m=0 and n=0)

(S)-1-hydroxy-2-tetrahydropyranyloxypropane (120 g, 0.75 mol) was dropwise added to sodium hydride (44.8 g, 1.87 mol) in THF (400 ml), followed by adding DMF (200 ml), agitating the mixture for 2 hours, dropwise adding to the mixture, butyl bromide (112.4 g, 0.82 mol) at 30° C. or lower, agitating the mixture at room temperature for 6 hours, adding toluene, sufficiently agitating the mixture, washing the resulting organic layer with 2N-NaOH aqueous solution and then with water, drying it over anhydrous magnesium sulfate, distilling off toluene, adding to the resulting oily residue, pyridium p-toluenesulfonate (18 g) and ethanol (500 ml), heating the mixture at 70° C. for one hour, distilling off ethanol, adding toluene to the residue, sufficiently washing the mixture with water, distilling off toluene and distilling the residue to obtain (S)-1-butyloxy-2-hydroxypropane (79.3 g) (b.p. 87° C./35 mmHg) ($\alpha_D^{24} = +3.6$ (l=1.0 dm neat)).

A mixture of this (S)-1-butyloxy-2-hydroxypropane (47.6 g, 0.36 mol) with anhydrous pyridine (300 g) was cooled with ice, followed by dropwise adding thereto a solution of p-toluenesulfonyl chloride (75.8 g, 0.20 mol) in pyridine (70 ml) at 0° C., agitating the mixture at room temperature for 3 hours, adding toluene (800 ml), agitating the mixture, several times washing the resulting organic layer with water, drying it over anhydrous magnesium sulfate and distilling off toluene to obtain (S)-1-butyloxy-2-(p-toluenesulfonyloxy)propane (93.1 g). A solution of 4-hydroxy-4'-octyloxybiphenyl (10 g, 0.017 mol) in THF (20 ml) was dropwise added to a mixture of sodium hydride (0.85 g, 0.035 mol) with THF (10 ml), followed by further dropwise adding a solution of the above (S)-1-butyloxy-2-(p-toluenesulfonyloxy)-propane (5.7 g, 0.02 mol) in DMF (10 ml), agitating the mixture at 60° C. for 4 hours, allowing it to cool down, adding toluene, agitating the mixture, washing with 6N-HCl, then with 2N-NaOH aqueous solution and further with water, drying over anhydrous magnesium sulfate, distilling off toluene and recrystallizing the residue from ethanol (100 ml) to obtain (R)-4-(2'-butyloxy-1'-methyl)ethyloxy-4'-octyloxybiphenyl (8.2 g) (m.p. 39.6° C.).

EXAMPLE 7 (USE EXAMPLE 1)

A liquid crystal composition consisting of the following achiral smectic liquid crystal compounds was prepared:

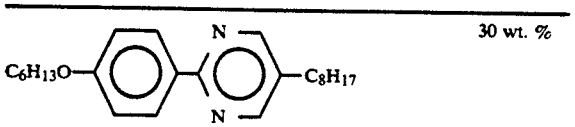

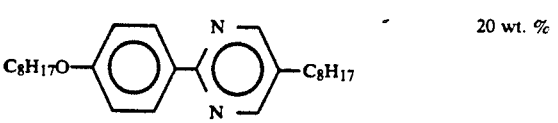

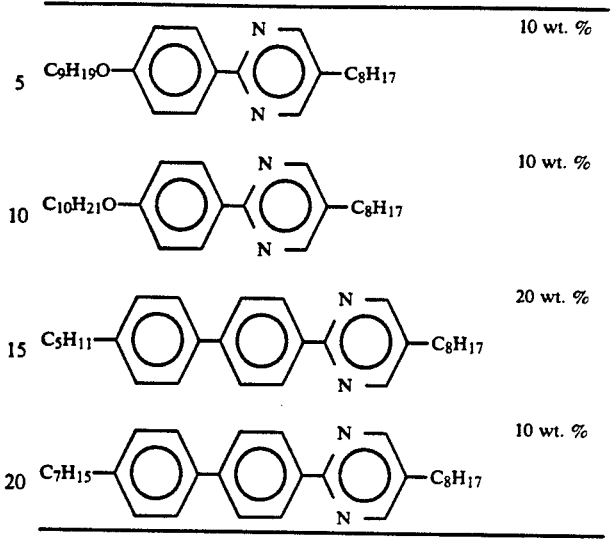

This liquid crystal composition exhibits the following phase transition points:

A liquid crystal composition consisting of the above liquid crystal composition (80% by weight) and the compound of Example 4 as a compound of the formula (I) of the present invention (20% by weight) was prepared. This composition was a chiral smectic liquid crystal composition having the following phase transition points:

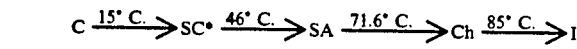

This chiral smectic liquid crystal composition was filled in a cell of 2 μm thickness provided with transparent electrodes each obtained by coating PVA (polyvinyl alcohol) onto the surface and rubbing the resulting surface to subject it to a parallel aligning treatment, followed by placing the resulting liquid crystal element between a polarizer and an analyzer crossed to each other and impressing a voltage of 15 V. As a result, change in the intensity of transmitted light was observed, and the response time was sought from the change to give 125 μsec at 25° C. Further, the spontaneous polarization value Ps of this liquid crystal composition was 2 nC/cm² and its tilt angle was 14°.

As described above, when the compound of the formula (I) of the present invention is added as a component to a non-optically active liquid crystal composition, a ferroelectric chiral smectic liquid crystal composition having a high response rate is obtained.

EXAMPLE 8 (USE EXAMPLE 2)

A nematic liquid crystal composition consisting of

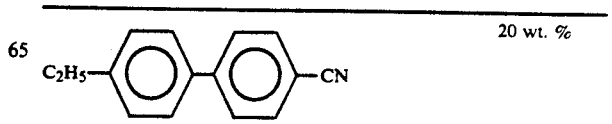

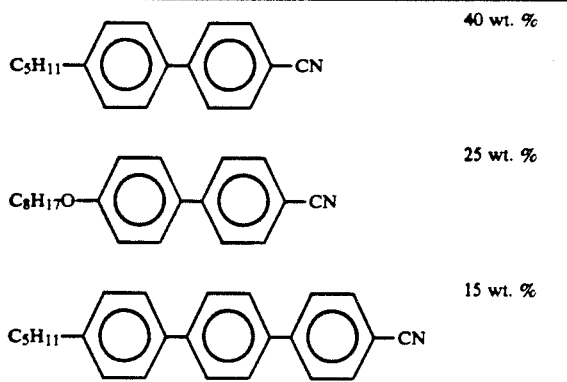

was filled in a cell having a distance between electrodes of 10 μm to prepare a TN type display cell, which was observed under a polarizing microscope. As a result, formation of reverse twist domain was observed. In addition, the used cell was prepared by coating PVA onto the surface and rubbing the resulting surface to subject it to a parallel aligning treatment.

To the above nematic liquid crystal composition was added a compound of the present invention

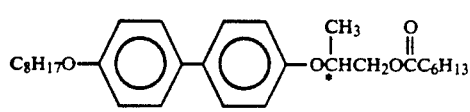

in an amount of 0.1% by weight, and the same TN type cell as above was prepared and observed. As a result, the reverse twist domain was dissolved and a uniform nematic phase was observed.

What we claim is:

1. An optically active compound expressed by the formula

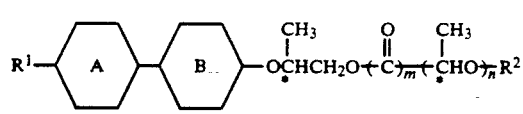

wherein $R^1$ represents an alkyl group or alkoxy group each of 6 to 9 carbon atoms;

represents

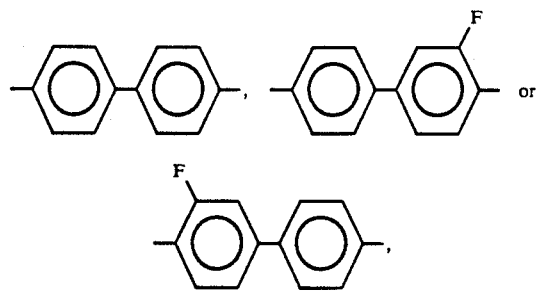

$R^2$ represents an alkyl group of 4 to 7 carbon atoms; and m and n each represent 0 or 1.

2. An optically active compound according to claim 1, wherein m=1 and n=0.

3. An optically active compound according to claim 1, wherein said

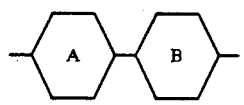

represents

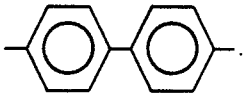

4. An optically active compound according to claim 1, wherein m=1 and n=1.

5. An optically active compound according to claim 1, wherein m=0 and n=0.

6. A chiral liquid crystal composition comprising at least two components at least one of which is an optically active compound as set forth in claim 1.

7. A chiral liquid crystal composition according to claim 6, exhibiting a chiral smectic phase.

8. A chiral liquid crystal composition according to claim 6, exhibiting a chiral nematic phase.

* * * * *